United States Patent [19]

Konrad et al.

[11] Patent Number: 4,994,087
[45] Date of Patent: Feb. 19, 1991

[54] COMPOUNDS CONTAINING SUBSTITUTED PHENYLAMINO AND PYRIDYL GROUPS AND HAIR DYEING PREPARATIONS USING THEM

[75] Inventors: Guenther Konrad, Hilden; Edgar Lieske, Duesseldorf, both of Fed. Rep. of Germany

[73] Assignee: Henkel Kommanditgesellschaft auf Aktien, Duesseldorf, Fed. Rep. of Germany

[21] Appl. No.: 280,109

[22] Filed: Dec. 5, 1988

[30] Foreign Application Priority Data

Dec. 5, 1987 [DE] Fed. Rep. of Germany ....... 3741236

[51] Int. Cl.$^5$ ..................... A61K 7/13; C07D 213/73; C07D 213/38
[52] U.S. Cl. .......................................... 8/409; 8/408; 8/411; 8/416; 8/423; 546/304; 546/307; 546/311; 546/329; 546/334
[58] Field of Search ................ 546/304, 329, 334, 307, 546/311; 514/352, 357; 8/408, 409, 416, 423, 411

[56] References Cited

U.S. PATENT DOCUMENTS 3,647,351 3/1972 Lange ...................... 8/10.2
3,933,988 12/1975 Welstead, Jr. et al. ............. 546/329

FOREIGN PATENT DOCUMENTS 3137473 4/1983 Fed. Rep. of Germany ...... 560/261
45-11500 4/1970 Japan ................................... 546/329
1178012 1/1970 United Kingdom ................ 546/329

OTHER PUBLICATIONS

Fette, Seifen, Anstrichmittel 67. Jahrg., (1965), p. 222.
Fette, Seifen, Anstrichmittel 69. Jahrg., (1967), pp. 348–352.
Zviak, *The Science of Hair Care*, vol. 7, pp. 263–268.

Primary Examiner—Robert W. Ramsuer
Assistant Examiner—Zinna Northington Davis
Attorney, Agent, or Firm—Ernest G. Szoke; Wayne C. Jaeschke; Norvell E. Wisdom, Jr.

[57] ABSTRACT

Novel compounds with structures corresponding to the formula:

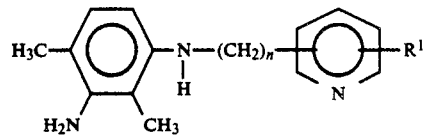

in which $n=0$ or 1 and $R^1$ is hydrogen, a $C_1$–$C_4$ alkyl or hydroxyalkyl group, or an amino group, and salts of such compounds, are superior to previously known couplers for oxidation hair dyes to produce a variety of colors, especially reds, when used with standard developer components. With 2,4,5,6-tetraaminopyrimidine developer for example, these novel compounds produce red to brown hair colors and, with p-tolylenediamine developer, red to blue-violet hair colors.

20 Claims, No Drawings

COMPOUNDS CONTAINING SUBSTITUTED PHENYLAMINO AND PYRIDYL GROUPS AND HAIR DYEING PREPARATIONS USING THEM

FIELD OF THE INVENTION

This invention relates to hair-dyeing preparations based on oxidation dyes and to novel organic compounds useful in such preparations. Hair-dyeing preparations of the type in question contain oxidation dye precursors in a cosmetic carrier. The oxidation dye precursors used are developer substances and coupler substances which form dyes under the effect of oxidizing agents or atmospheric oxygen. The cosmetic carriers used for the oxidation dye precursors are creams, emulsions, gels, shampoos, foam aerosols or other preparations suitable for application to the hair.

STATEMENT OF RELATED ART

By virtue of their intense colors and good fastness properties, so-called oxidation dyes, which are formed by the oxidative coupling of one or more developer components with one another or with one or more coupler components, play a prominent part in the dyeing of hair. The definitive characteristic of a developer is the ability to be converted by chemical oxidation into an intensely colored substance with reasonable stability. This quality is usually achieved by the presence in the developer molecules of phenyl, pyridyl, or pyrimidyl rings having at least one primary amino substituent and at least one additional strong or moderately strong electron releasing substituent, such as amino, alkyl substituted amino, hydroxyl, alkyl substituted hydroxyl, or the like, in a position ortho or para to the primary amino substituent, thereby favoring oxidation to a quinoid structure that is highly colored. Heterocyclic hydrazone derivatives and 4-aminopyrazolone derivatives are also known developers.

As noted above, materials suitable as developers can be mixed with each other to produce modified colors. More commonly, however, developers are used together with other materials that are not suitable as developers themselves but that do modify the colors achieved with developers in desirable ways. These materials are denoted herein, and in the art generally, as "couplers". Most couplers have molecular structures that incorporate the same aromatic or psuedo-aromatic rings and substituents as noted above for developers, but with the important difference that the two electron-releasing substituents are in positions meta to each other, so that no quinoid structure is produced by oxidation. Thus, common couplers are m-phenylene-diamine derivatives, naphthols, resorcinol derivatives and pyrazolones.

A wide variety of possible substituents on the basic developer and coupler molecular structures are possible, but it is not possible in advance to know which such substituents will give desirable results when used in practical hair dyes. Good oxidation dye precursors need to satisfy the following major requirements: They must form the required shades with sufficient intensity during the oxidative coupling reaction. In addition, they must be readily absorbed by human hair without excessively staining the scalp. Dye absorption should also be uniform, i.e. the more heavily stressed ends should not be dyed to a greater extent than the less damaged hair nearest the skin, often called "roots". The hair colors produced should be highly stable to heat, light and the chemicals used in the permanent waving of hair. Finally, the oxidation hair dye precursors should be safe to use from the toxicological and dermatological viewpoint.

Aminopyridine derivatives are known as oxidation dye precursors, for example from *Fette, Seifen, Anstrichmittel* vol. 67 (1965), page 222 and vol. 69 (1967), pages 348–352 and from U.S. Pat. No. 3,647,351. 2,4-Diamino-m-xylenes are also already known as couplers for oxidation dyes from DE-A-31 37 473. However, the hair-dye preparations obtainable with the known couplers and developers are unsatisfactory in regard to the fastness properties of the hair colors obtained with them. In particular, the known aminopyridines and 2,4-diamino-m-xylenes are not suitable as red couplers for developer components of the p-phenylenediamine derivative type (particularly m-phenylenediamine and p-tolylenediamine), either because they do not form red shades with developers of this type or because the colors formed are not uniformly absorbed on the hair roots and hair ends. Commercially useful red couplers have hitherto not been available at all for these developers.

DESCRIPTION OF THE INVENTION

Except in the operating examples, or where otherwise specified, all numerical quantities in this description specifying amounts of ingredients or reaction conditions are to be understood as modified by the word "about".

New aminopyridine derivatives which are suitable as red couplers for p-phenylenediamine, p-tolylenediamine and derivatives of these known developer compounds and which show surprisingly good performance properties have now been found. These new compounds suitable for couplers either themselves have, or are salts of compounds that have, the structural formula, hereinafter called Formula I:

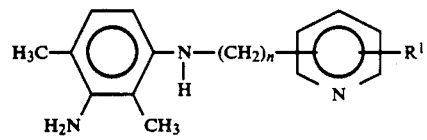

in which $n=0$ or 1 and $R^1$ is hydrogen, a $C_1$–$C_4$ alkyl or hydroxyalkyl group, or an amino group. The two substituents on the pyridine nucleus in Formula I may occupy any positions relative to one another and to the heteroatom in the ring.

The compounds corresponding to Formula I are very effective as couplers for a number of known developer compounds and produce particularly brilliant colors characterized by high light and heat stability. The developers present in the hair-dyeing preparations according to the invention can be, for example, aromatic amines containing one or more $NH_2$ groups, NHR groups, $NR_2$ groups, where R is a $C_1$–$C_4$ alkyl group or a hydroxyalkyl group or a $C_2$–$C_4$ aminoalkyl group, amino-phenols, aminophenol ethers, diaminopyridine derivatives or 2,4,5,6-tetraaminopyrimidine and derivatives thereof.

Compounds of Formula I in which $R^1$ is hydrogen or an amino group are generally preferred.

The compounds corresponding to Formula I are new, but they may be obtained from known starting materials by methods known per se in preparative chemistry.

Thus, 3-amino-2,4-dimethylphenylaminopyridines corresponding to Formula I, in which n=0, can be readily obtained by reaction of 2,4-dimethyl-m-phenylenediamine or 2,4-dimethyl-3-nitroaniline with a compound corresponding to the following formula, hereinafter denoted Formula II:

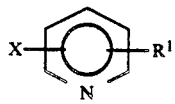

in which X is chlorine or bromine and $R^1$ is hydrogen, a $C_1$-$C_4$ alkyl or hydroxyalkyl group or a nitro group, in the presence of a strong base, then catalytically hydrogenating any nitro groups present in the reaction product to amino groups.

Compounds corresponding to Formula I when n=1 can readily be obtained by condensing 2,4-dimethyl-3-nitroaniline with a pyridine aldehyde corresponding to the following formula, hereinafter denoted Formula III:

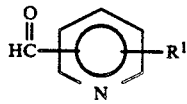

in which $R^1$ has the same meaning as before, to form the corresponding Schiff's base, and then catalytically hydrogenating the azomethine group and the nitro groups at the same time.

Examples of the preparation of compounds according to the invention corresponding to Formula I, in which n=0, is described in detail in Example 1.1 to 1.3 while the production of compounds corresponding to Formula I, in which n=1, is described in detail in Examples 1.4 to 1.6.

The present invention also relates to hair-dyeing preparations containing oxidation dye precursors in a suitable cosmetic carrier, the oxidation dye precursors comprising compounds having general Formula I as couplers, along with a known developer and, optionally, previously known coupler components.

Among the compounds of Formula I according to the invention, those in which n =0 are particularly suitable for the hair-dyeing preparations according to the invention. Among the known developers, those which form red, red-brown or red-violet shades with the couplers according to the invention are particularly suitable: such developers are primarily p-phenylenediamine, p-tolylenediamine and derivatives thereof. However, the compounds of Formula I according to the invention can be used with any of the following developers: 1,4-diaminobenzene, 1,4-diamino-2-chlorobenzene, 4-aminodiphenyl amine, 1-hydroxy-2-aminobenzene, 1-hydroxy-4-aminobenzene, 1,2-diaminobenzene, 1-methyl-2,5-diaminobenzene, 1-hydroxy-4-methylaminobenzene, 3,4-diaminobenzoic acid, 1-methyl-2,3-diaminobenzene, 1-methoxy-2,5-diaminobenzene, 1-amino-4-diethylaminobenzene, 1,3-dimethyl-2,5-diamino-4-methoxy benzene, 1-amino-4-methylamino benzene, 1-phenyl-3-methylpyrazol-5-one, 1-amino-4-[(2-methoxyethyl)amino]benzene, 1-amino-4-dimethylamino benzene, 1-amino-4[di(2-hydroxyethyl-)amino] benzene sulfate, 2,4,5,6-tetraamino pyrimidine, 4,5,6-triamino-2-dimethylamino-1,3-diazine, 1-amino-4[ethyl(2-hydroxyethyl)amino]benzene; 1-amino-4[(2,3-dihydroxyprophy)amino]benzene, 1-hydroxy-2,5-diamino-4-methyl benzene, 1-hydroxy-2,6-diamino-4-(diethylamino) benzene,1,3-diamino-2,5-dihydroxybenzene,1-hydroxymethyl-2,5-diamino benzene, 1-hydroxy-3-methyl-4-amino benzene, 1-hydroxy-2-amino-5-methyl benzene, 1-(2-hydroxyethyl)-2,5-diaminobenzene, 4,4'-diaminodiphenyl amine, 1,3-dimethyl-2,5-diaminobenzene, 1,4-diamino-2(2-propyl)-benzene, 1-amino-4-[(2-hydroxypropyl)amino]benzene, and 1-hydroxy-2-amino-6-methylbenzene.

The compounds according to Formula I can be introduced into the hair-dyeing preparations according to the invention either in free form or in the form of salts of the amino groups with inorganic or organic acids, for example in the form of the hydrochlorides, sulfates, phosphates, acetates, propionates, lactates or citrates.

In addition to the compounds corresponding to Formula I, the hair-dyeing preparations according to the invention can also contain other known couplers which are useful for modifying the shades and for producing natural hues. Known couplers of the type in question include, for example, 1-methoxy-2,4-diaminobenzene, 1,2-dihydroxybenzene, 1,3-dihydroxybenzene, 1,3-dihydroxy-4-chlorobenzene, 1,2,3-trihydroxybenzene, 1-hydroxy-3-aminobenzene, 1-hydroxynapthalene, 1,5-dihydroxynaphthlene, 2,7-dihydroxynaphthalene, 1-hydroxy-2,4-diaminobenzene, 1,7-dihydroxynaphthalene, 1,3-diaminobenzene, 1-methyl-2,4-diaminobenzene, 1,4-dihydroxybenzene, 1-methyl-2-hydroxy-4(carbamoylmethylamino)benzene, 1-hydroxy-3-(carbamoylmethylamino)benzene, 6-hydroxybenzomorpholine,1-hydroxy-3dimethylaminobenzene, 1-methyl-2-hydroxy-4-aminobenzene, 6-hydroxyquinoline,1-methyl-2-hydroxy-4-[(2-hydroxyethyl)amino]benzene, 1-methyl-2,4,5-trihydroxybenzene, 1,2,4-trihydroxybenzene, 1,3-dimethyl-2-hydroxy-4-acetamidobenzene, 1,3-diamino-4-(2-hydroxyethoxy)benzene, 1-amino-2,6-dichloro-3-hydroxybenzene, 1,3-dihydroxy-2-methylbenzene, 1-ethyl-2-methoxy-3,5-diaminobenzene, 1-hydroxy-6-aminonaphthalene-3-sulfonic acid, 6-methoxy-8-aminoquinoline, 2,6-dihydroxy-4-methylpyridine, 1,3-diamino-4-methoxy-5-methylbenzene, 2,3-dihydroxynapthalene, 1-3-dihydroxy-5-methylaminobenzene, 1-ethoxy-2,4-diaminobenzene, 5-hydroxy-1,4-benzodioxane, 1-hydroxy-3-amino-4,6-dichlorobenzene, 1,4-dihydroxy-2-aminobenzene, 1,4-dihydroxy-2-methylaminobenzene, 1-hydroxy-2-amino-4-methoxybenzene, 6-aminobenzomorpholine, 1-amino-3-[di(2-hydroxyethyl)amino] benzene, 1-methyl-2,6-diaminobenzene, 1-hydroxy-2,4-diamino-6-methylbenzene, 1-hydroxy-2-amino-4-methylamino benzene, 1-hydroxy-3-ethylamino-4methylbenzene, 1-hydroxy-3-diethylaminobenzene, 1-hdroxy-2-(2propyl)-5-methylbenzene, 1-amino-3[di(2-hydroxyethyl)amino]-4-ethoxy benzene, di(2,4-diaminophenoxy)methane, 1,3-di(2,4-diaminophenoxy)propane, 1-(2-hydroxyethyl)-2,4-diamino benzene, 1-hydroxy-3,4-methylenedioxybenzene, 1,5-dihydroxy-1,2,3,4-tetrahydronaphthalene, 1-methoxy-2-amino-4(2-hydroxyethyl)aminobenzene, 1-(2-aminoethoxy)-2,4-diaminobenzene, 1-(2-hydroxethoxy)-2-amino-4-methylamino benzene, 1,3-dihydroxy-2-chlorobenzene, 1,3-dihydroxy-2-methyl-5,6-dichlorobenzene, 1-hydroxy-2-methyl-3-amino benzene, (2,4-diaminophenoxy)acetic acid, 1-amino-2-chloro-3-hydroxy-4-methylbenzene, 1-amino-4-(2-hydroxyporpyl)amino benzene,1-hydroxy-2,4-dichloro- 3-(2-propylidene)amino benzene, 1-(2-hydroxyethyl)amino-3,4-methylenedioxybenzene, 2,6-dihydroxy-3,4-dimethylpyridine, 2,4-diaminophenyl-2-hydroxyethyl ether, 1-methoxy-2,4-diaminobenzene, and pyrazolenes.

Substantive dyes may also be additionally used for further modifying the shades of color achieved. Suitable substantive dyes are, for example, nitrophenylenediamines, nitroamino-phenols, anthraquinone dyes or indophenols.

To prepare the hair-dyeing preparations according to the invention, the new couplers corresponding to Formula I and the known couplers additionally present, if any, are generally used in quantities such that the sum of the number of moles of couplers approximately equals the total number of moles of the developer components used. Although it is preferred to use equimolar quantities, a modest excess of either coupler or developer is not a significant disadvantage, so that developer components and coupler components may be present in a molar ratio of from 1:0.5 to 1:2.

The new couplers corresponding to Formula I and the other oxidation dye precursors or substantive dyes otherwise present in the hair-dyeing preparations do not have to be pure, individual chemical compounds, but can be mixtures of individually suitable components.

Most simply, the hair color may be oxidatively developed from the coupler and developer components by atmospheric oxygen. However, it is usually preferred to use a chemical oxidizing agent, particularly when it is desired not only to color, but also to lighten the hair. Particularly suitable oxidizing agents are hydrogen peroxide or adducts thereof with urea, melamine or sodium borate and also mixtures of such hydrogen peroxide adducts with potassium peroxydisulfate.

To produce the hair-dyeing preparations according to the invention, the oxidation dye precursors are incorporated in a suitable cosmetic carrier. Examples of suitable cosmetic carriers are creams, emulsions, gels and surfactant-containing foaming solutions, for example, shampoos or other preparations which are suitable for application to the hair. Normal ingredients of cosmetic preparations such as these are, for example, (i) wetting agents and emulsifiers, such as anionic, nonionic or ampholytic surfactants, e.g., alcohol sulfates, alkanesulfonates, α-olefin sulfonates, alcohol polyglycol ether sulfates, ethylene oxide adducts with alcohols, acids and alkylphenols, sorbitan acid esters and acid partial glycerides, and acid alkanolamides, all preferably characterized by the presence in the molecular structure of a $C_{12}$–$C_{18}$ a straight chain alkyl group; (ii) thickeners, for example methyl or hYdroxyethyl cellulose and starch; (iii) natural or synthetic hydrocarbon oils and waxes, alcohols, amides, and esters, all preferably containing a straight chain $C_{12}$–$C_{18}$ alkyl group and all substantially water-insoluble; (iv) perfume oils; and (v) hair care additives that promote the health of the hair or make it more attractive in some manner not connected with color or make it easier to care for, such as by reducing its tendency to electrostatic charging, making combing easier, maintaining its shape, or the like; for example, water-soluble cationic polymers, protein derivatives, pantothenic acid and cholesterol.

The constituents of the cosmetic carriers are used in the usual quantities in the production of hair-dyeing preparations according to the invention. For example, emulsifiers are used in concentrations of 0.5 to 30% by weight and thickeners in concentrations of 0.1 to 25% by weight, based on the hair-dyeing preparations as a whole.

A particularly suitable carrier is an oil-in-water emulsion containing 0.1 to 25% by weight of (i) alcohols, hydrocarbons, and/or esters, all containing a straight chain $C_{12}$–$C_{18}$ alkyl group and (ii) 0.5 to 30% by weight of an emulsifier from the group of anionic, nonionic or ampholytic surfactants.

The oxidation dye precursors are preferably incorporated in the carrier in quantities of 0.2 to 5% by weight and more preferably in quantities of 1 to 3% by weight, based on the hair-dyeing preparation as a whole. The content of one or more compounds according to Formula I in hair-dyeing preparations according to this invention can preferably be from 0.05 to 10 millimole per 100 g of the hair-dyeing preparation.

Highly preferred carrier formulation for the compounds of Formula I according to the invention are cream hair dyes in the form of an oil-in-water emulsion containing:

(i) 1–10 millimole of developer components per 100 g,
(ii) 1 to 10 millimole of coupler components per 100 g,
(iii) 1 to 10% by weight of a $C_{10}$–$C_{18}$ alkyl sulfate or a $C_{10}$–$C_{16}$ alkyl ether sulfate surfactant, (iv) 5 to 20% by weight of $C_{12}$–$C_{18}$ straight chain alcohols,
(v) 0.1 to 2% by weight of an oxidation inhibitor, most preferably from the group consisting of alkali sulfite, alkali ascorbate, and alkali dithionite, and
(vi) ammonia in a quantity sufficient to adjust the pH of the emulsion to a value of 8 to 10.

The alkyl sulfate or alkyl ether sulfate surfactant mentioned can be present as an alkali, ammonium, or alkanol ammonium salt containing 2 or 3 carbon atoms in the alkanol group, for example as the sodium, triethanolamine or isopropanol ammonium salt. A salt of a sulfuric acid mono ester of an adduct of 1 to 10 moles of ethylene oxide with a $C_{10}$–$C_{16}$ straight chain alcohol can be used as the alkyl $C_{10}$–$C_{16}$ ether sulfate surfactant.

The hair dyeing preparations according to the invention can be used in a mildly acidic, neutral, or alkaline medium, irrespective of the type of cosmetic carrier used, for example a cream, gel or shampoo. The hair-dyeing preparations are preferably used at a pH value in the range from 8 to 10 and at temperatures in the range from 15° C. to 40° C. After a contact time of about 30 minutes, the hair-dyeing preparation is removed by rinsing from the hair to be dyed. The hair is then washed with a mild shampoo and dried. Washing with a shampoo is unnecessary when a carrier of high surfactant content, for example a dye shampoo, is used.

The following Examples are intended to illustrate the invention without limiting it in any way.

1. PREPARATION EXAMPLES

1.1. 2-[(3-Amino-2,4-dimethylphenyl)-amino]-pyridine

Step 1: Synthesis of 2-[(3-nitro-2,4-dimethylphenyl)-amino]-pyridine.

3.3 g of 3-Nitro-2,4-dimethylaniline and 3.2 g of 2-bromo-pyridine are mixed and the resulting mixture heated for 8 hours to 170° C. After cooling to 20° C., the greasy mass formed was dissolved in water and the solution pH then raised by addition of sodium carbonate. The resulting precipitate was recrystallized from ethanol. 2 g of the product melting at 178° to 179° C. were obtained. Another 2.1 g of the substance were obtained from the aqueous phase by concentration.

Step 2: Reduction of the nitro group in the product of Step 1 amino.

3.7 g of the product from Step 1 were dissolved in 150 ml of an ethanol/water mixture (1:1 by volume) and the resulting solution hydrogenated in the presence of palladium (on active carbon) as catalyst. After 1.07 liter of hydrogen had been taken up, the solution was concentrated and the residue was taken up in dimethyl ether. 2.4 g of product melting at 132° to 135° C. were obtained after evaporation of the ether.

| Analysis: $C_{13}H_{15}N_3$ (MW: 213.3) | | | |
|---|---|---|---|
| | C | H | N |
| Calculated | 73.21 | 7.09 | 19.70 |
| Found | 73.10 | 7.19 | 19.30 |

1.2
2-[(3-amino-2,4-dimethylphenyl)-amino]-3-aminopyridine

Step 1: Synthesis of 2-[(3-nitro-2,4-dimethylphenyl)-amino]-3-aminopyridine.

8.4 g of 2,4-diamino-m-xylene, 9.6 g of 2-chloro-3-nitropyridine and 3.0 g of calcium carbonate were introduced into 300 ml water and the resulting mixture was heated under reflux for 8 hours to the boiling temperature. The reaction mixture was filtered while hot, the reaction product precipitating from the filtrate on cooling to 20° C. It was isolated and recrystallized from toluene. 6.2 g of the product melting at 173° to 175° C. were obtained.

| Analysis $C_{13}H_{14}N_4O_2$ (MW: 258.3) | | | | |
|---|---|---|---|---|
| | C | H | N | O |
| Calculated | 60.45 | 5.46 | 21.69 | 12.4 |
| Found | 60.40 | 5.32 | 22.1 | 12.0 |

Step 2: Reduction of the nitro group in the product of Step 1 to amino.

6.2 g of the product from Step 1 were dissolved in 150 ml of ethanol and the resulting solution hydrogenated in the presence of palladium (on active carbon) as catalyst. After 1.74 liter of hydrogen had been taken up, the solution was concentrated and 3.8 g of the product melting at 202° C. were obtained as residue.

| Analysis: $C_{13}H_{16}N_4$ (MW: 228.3) | | | |
|---|---|---|---|
| | C | H | N |
| Calculated | 68.39 | 7.07 | 24.54 |
| Found | 68.40 | 7.06 | 24.60 |

1.3
2-[(3-amino-2,4-dimethylphenyl)-amino]-aminopyridine trihydrochloride monohydrate Step 1: Synthesis of 2-[(3-amino-2,4-dimethyl)-amino]-5-nitropyridine.

4.2 g of 2,4-diamino-m-xylene and 4.8 g of 2-chloro-5-nitropyridine were heated under reflux for 8 hours in 200 ml water together with 3.5 g of potassium fluoride. The product precipitated after cooling was filtered off under suction, washed with water, and suspended in warm toluene. 4.5 g of a substance melting at 200° C. were obtained after refiltration under suction and drying. 3.2 g of product melting at 208° to 209° C. were obtained after recrystallization from toluene.

| Analysis: $C_{13}H_{14}N_4O_2$ (MW: 258.3) | | | |
|---|---|---|---|
| | C | H | N |
| Calculated | 60.45 | 5.46 | 21.69 |
| Found | 61.1 | 5.78 | 22.0 |

Step 2: Reduction of the nitro group in the product of Step 1 to amino.

2.4 g of the product from Step b 1 were reduced with hydrogen (uptake 0.655 liter) in 100 ml ethanol in the presence of Raney nickel as catalyst. After filtration, the mixture was rapidly acidified with hydrochloric acid and then concentrated by evaporation to dryness. 1.2 g of product were isolated.

| Analysis: $C_{13}H_{15}N_4.3HCl.H_2O$ (MW: 354.7) | | | | |
|---|---|---|---|---|
| | C | H | N | Cl |
| Calculated | 43.9 | 5.95 | 15.75 | 29.9 |
| Found | 43.7 | 5.56 | 15.1 | 29.7 |

1.4 2-{[(3-amino-2,4-dimethylphenyl)-amino]-methylene)}-pyridine trihydrochloride Step 1: Synthesis of 2-[(2,4-dimethyl-3-nitrophenylimino)-methylene]-pyridine.

3.3 g of 4-amino-2-nitro-m-xylene and 2.1 g of 2-pyridinealdehyde were dissolved in 50 ml ethanol and left to stand. Crystals slowly precipitated and were filtered off under suction and washed with ethanol. The dried product (3.0 g) had a melting point of 114° to 116° C.

| Analysis: $C_{14}H_{13}N_3O_2$ (MW: 255.3) | | | |
|---|---|---|---|
| | C | H | N |
| Calculated | 65.87 | 5.13 | 16.46 |
| Found | 65.7 | 5.04 | 16.3 |

Step 2: Reduction of the nitro and azomethine groups in the product of Step 1 to amino.

3.0 g of the product from Step 1 were hydrogenated (1 liter of $H_2$ uptake) in 150 ml ethanol in the presence of platinum (on active carbon) as catalyst. After reduction, the mixture was acidified with hydrochloric acid and concentrated by evaporation to dryness. 3.2 g of a highly hygroscopic product decomposing at 122° C. were obtained.

| Analysis: $C_{14}H_{17}N_3.3HCl$ (MW: 336.7) | | | |
|---|---|---|---|
| | C | H | N |
| Calculated | 49.94 | 5.99 | 12.48 |
| Found | 49.0 | 6.07 | 12.1 |

1.5
3-{[(3-amino-2,4-dimethylphenyl)-amino]-methylene}-pyridine trihydrochloride

Step 1: Synthesis of 3-{[(2,4-dimethyl-3-nitrophenylimino)]-methylene}pyridine.

3.6 g product melting at 138° to 142° C. were obtained as in Step 1 of 1.4 from 3.3 g of 4-amino-2-nitro-m-xylene and 2.1 g of 3-pyridinealdehyde.

| Analysis: $C_{14}H_{13}N_3O_2$ | | | |
|---|---|---|---|
| | C | H | N |
| Calculated | 65.87 | 5.13 | 16.46 |
| Found | 66.4 | 5.08 | 16.4 |

Step 2: Reduction of the nitro and azomethine groups in the product of Step 1 to amino.

After acidification with hydrochloric acid and concentration by evaporation to dryness, the reduction of 3.6 g of the product from Step 1 with hydrogen in 150 ml ethanol in the presence of palladium (on active carbon) as catalyst (1.32 liter of $H_2$ uptake) yielded 3.6 g of a highly hygroscopic substance melting beyond 175° C.

| Analysis: $C_{14}H_{17}N_3.3HCl.H_2O$ (MW: 354.7) | | | |
|---|---|---|---|
| | C | H | N |
| Calculated | 47.41 | 6.25 | 11.85 |
| Found | 46.9 | 5.82 | 11.8 |

1.6
4-{[(3-amino-2,4-dimethylphenyl)-amino]-methylene}-pyridine trihydrochlodride dihydrate

Step 1: Synthesis of 4-[(2,4-dimethyl-3-nitrophenylimino)-methylene]-pyridine.

2.3 g of product melting at 111° to 113° C. were obtained as in Step 1 of 1.4 from 3.3 g 4-amino-2-nitro-m-xylene and 2.1 g 4-pyridinealdehyde.

| Analysis: $C_{14}H_{13}N_3O_2$ | | |
|---|---|---|
| | C | H |
| Calculated | 65.87 | 5.13 |
| Found | 66.3 | 5.29 |

Step 2: Reduction of the nitro and azomethine groups in the product of Step 1 to amino.

Reduction with hydrogen of 2.3 g of product from Step 1 dissolved in 150 ml of ethanol, in the presence of palladium-on-activated-carbon catalyst, resulted in uptake of 0.85 liter of $H_2$. After acidification of the hydrogenated solution with hydrochloric acid and concentration by evaporation to dryness, 2.3 g of a hygroscopic product was obtained.

| Analysis: $C_{14}H_{17}N_3.3HCl.2H_2O$ | | | |
|---|---|---|---|
| | C | H | N |
| Calculated | 45.12 | 6.49 | 11.27 |
| Found | 45.10 | 6.08 | 11.10 |

2. Hair-Dyeing Preparation Examples

Hair-dyeing preparations according to the invention were prepared in the a carrier of cream emulsion. The preparations had the following composition:

| | |
|---|---|
| $C_{12}-C_{18}$ straight chain alcohol | 10 g |
| 28 weight % solution in water of the sodium salt of a mono-ester with sulfuric acid of the product of condensation of a $C_{12}-C_{14}$ straight chain alcohol with an average of 2 moles of ethylene oxide per mole of alcohol | 25 g |
| Water | 60 g |
| Developer component (component D) | 7.5 mmol |
| Coupler component (component C) | 7.5 mmol |
| $Na_2SO_3$ (inhibitor) | 1.0 g |
| Sufficient concentrated aqueous ammonia solution to give pH = 9.5 | |
| Water to give a total of 100 g. | |

The constituents were mixed together in the order listed above. After addition of the oxidation dye precursors and the inhibitor, the pH value of the emulsion was first adjusted to 9.5 with concentrated ammonia solution, after which the emulsion was made up with water to 100 g.

The hair color was oxidatively developed with 3% hydrogen peroxide solution as oxidizing agent. To this end, 50 g hydrogen peroxide solution (3%) were added to and mixed with 100 g of the emulsion.

The resulting dye cream was applied to approximately 5 cm strands of standardized, 90 % grey, but not specially pretreated human hair and left thereon for 30 minutes at 27° C. After dyeing, the hair was rinsed, washed with a standard shampoo and then dried.

The following compounds were used as developer components:

D 1: 2,4,5,6 tetraaminopyrimidine sulfate
D 2: p-tolylenediamine sulfate
D 3: p-phenylenediamine
D 4: p-aminophenol
D 5: N,N-dimethyl-p phenylenediamine sulfate.
D 6: $N^1$-(2-methanesulfonamido) ethyl-3-methyl-p-phenylenediamine sesquisulfate
D 7: $N^1$-ethyl-$N^1$-(2-hydroxyethyl) p-phenylenediamine sulfate
D 8: 2-chloro-p-phenylenediamine
D 9: 2,5-diaminoanisole sulfate The products of Example 1.1 to 1.6 according to the invention, as described above, were used as the coupler components (C 1.1 to C 1.6).

The hair colors obtained with these oxidation dye precursors in various combinations are shown in Table I.

TABLE I

| Application Example | Developer component | Coupler component | Shade obtained |
|---|---|---|---|
| 2.1 | D 1 | C 1.1 | red-blond |
| 2.2 | D 1 | C 1.2 | red-haired |
| 2.3 | D 1 | C 1.3 | olive-brown |
| 2.4 | D 1 | C 1.4 | red-haired |
| 2.5 | D 1 | C 1.5 | camel-brown |
| 2.6 | D 1 | C 1.6 | gold-brown |

TABLE I-continued

| Application Example | Developer component | Coupler component | Shade obtained |
|---|---|---|---|
| 2.7 | D 2 | C 1.1 | violet |
| 2.8 | D 2 | C 1.2 | dark red-brown |
| 2.9 | D 2 | C 1.3 | dark purple |
| 2.10 | D 2 | C 1.4 | red-brown |
| 2.11 | D 2 | C 1.5 | purple |
| 2.12 | D 2 | C 1.6 | blue-violet |
| 2.13 | D 3 | C 1.3 | dark purple |
| 2.14 | D 4 | C 1.4 | dark violet |
| 2.15 | D 5 | C 1.5 | violet-brown |
| 2.16 | D 6 | C 1.6 | dark violet |
| 2.17 | D 7 | C 1.7 | violet ruby |
| 2.18 | D 8 | C 1.8 | dark blue |

What is claimed is:

1. A compound having the formula:

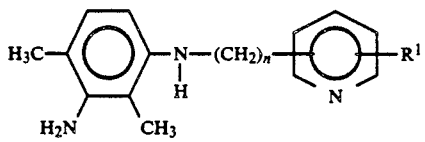

in which n is 0 or 1 and $R^1$ is hydrogen, $C_1-C_4$ alkyl, hydroxyalkyl, or an amino group; and the acceptable salts thereof.

2. Compounds according to claim 1, wherein $R^1$ is hydrogen or an amino group.

3. Compounds according to claim 2, wherein n is zero.

4. Compounds according to claim 1, wherein n is zero.

5. In a hair dyeing preparation comprising at least one coupler component and at least one developer component in a suitable cosmetic carrier, the improvement wherein said at least one coupler component comprises a compound according to claim 4.

6. In a hair dyeing preparation comprising at least one coupler component and at least one developer component in a suitable cosmetic carrier, the improvement wherein said at least one coupler component comprises a compound according to claim 3.

7. In a hair dyeing preparation comprising at least one coupler component and at least one developer component in a suitable cosmetic carrier, the improvement wherein said at least one coupler component comprises a compound according to claim 2.

8. In a hair dyeing preparation comprising at least one coupler component and at least one developer component in a suitable cosmetic carrier, the improvement wherein said at least one coupler component comprises a compound according to claim 1.

9. A hair dyeing preparation according to claim 8, wherein said one developer component comprises a compound selected from the group consisting of 2,4,5,6-tetraaminopyrimidine and salts thereof, p-tolylendiamine and salts thereof, p-phenylenediamine and salts thereof, NB,N-dimethyl-p-phenylenediamine and salts thereof, $N^1$-(2-methanesulfonamido)-ethyl-3-methyl-p-phenylenediamine and salts thereof, $N^1$-ethyl-$N^1$-(2-hydroxyethyl)-p-phenylenediamine and salts thereof, 2-chloro-p-phenylenediamine and salts thereof, and 2,5-diaminoanisole and salts thereof.

10. A hair dyeing preparation according to claim 7, wherein said one developer component comprises a compound selected from the group consisting of 2,4,5,6-tetraaminopyrimidine and salts thereof, p-tolylendia-mine and salts thereof, p-phenylenediamine and salts thereof, N,N-dimethyl-p-phenylenediamine and salts thereof, $N^1$-(2-methanesulfonamido)-ethyl-3-methyl-p-phenylenediamine and salts thereof, $N^1$-ethyl-$N^1$-(2-hydroxyethyl)-p-phenylenediamine and salts thereof, 2-chloro-p-phenylenediamine and salts thereof, and 2,5-diaminoanisole and salts thereof.

11. A hair dyeing preparation according to claim 6, wherein said one developer component comprises a compound selected from the group consisting of 2,4,5,6-tetraaminopyrimidine and salts thereof, p-tolyenedia-mine and salts thereof, p-phenylenediamine and salts thereof, N,N-dimethyl-p-phenylenediamine and salts thereof, $N^1$-(2-methanesulfonamido)-ethyl-3-methyl-p-phenylendiamine and salts thereof, $N^1$-ethyl-$N^1$-(2-hydroxyethyl)-p-phenylenediamine and salts thereof, 2-chloro-p-phenylenediamine and salts thereof, and 2,5-diaminoanisole and salts thereof.

12. A hair dyeing preparation according to claim 5, wherein said one developer component comprises a compound selected from the group consisting of 2,4,5,6-tetraaminopyrimidine and salts thereof, p-tolylenedia-mine and salts thereof, p-phenylenediamine and salts thereof, N,N-dimethyl-p-phenylenediamine and salts thereof, $N^1$-(2-methanesulfonamido)-ethyl-3-methyl-p-phenylenediamine and salts thereof, $N^1$-ethyl-$N^1$-(2-hydroxyethyl)-p-phenylenediamine and salts thereof, 2-chloro-p-phenylenediamine and salts thereof, and 2,5-diaminoanisole and salts thereof.

13. In a hair dyeing preparation comprising at least one coupler component and at least one developer component in a suitable cosmetic carrier, the improvement wherein (a) said at least one coupler component comprises a compound according to claim 4 in a quantity of 0.05 to 10 millimole per 100 g of the hair dyeing preparation, (b) said at least one developer component comprises a compound selected from the group consisting of 2,4,5,6-tetraaminopyrimidine and salts thereof, p-tolylenediamine and salts thereof, p-phenylenediamine and salts thereof, N,N-dimethyl-p-phenylenediamine and salts thereof, $N^1$-(2-methanesulfonamido)-ethyl-3-methyl-p-phenylenediamine and salts thereof, $N^1$-ethyl-$N^1$-(2-hydroxyethyl)-p-phenylenediamine and salts thereof, 2-chloro-p-phenylenediamine and salts thereof, and 2,5-diaminoanisole and salts thereof, and (c) the ratio between the number of moles of all coupler components and the number of moles of all developer components is between about 0.5 and about 2.

14. In a hair dyeing preparation comprising at least one coupler component and at least one developer component in a suitable cosmetic carrier, the improvement wherein (a) said at least one coupler component comprises a compound according to claim 3 in a quantity of 0.05 to 10 millimole per 100 g of the hair dyeing preparation, (b) said at least one developer component comprises a compound selected from the group consisting of 2,4,5,6-tetraaminopyrimidine and salts thereof, p-tolylenediamine and salts thereof, pphenylenediamine and salts thereof, N,N-dimethyl-p-phenylenediamine and salts thereof, $N^1$-(2-methanesulfonamido)-ethyl-3-methyl-p-phenylenediamine and salts thereof, $N^1$-ethyl-$N^1$-(2-hydroxyethyl)-p-phenylenediamine and salts thereof, 2-chloro-pphenylenediamine and salts thereof, and 2,5-diaminoanisole and salts thereof, and (c) the ratio between the number of moles of all coupler components and the number of moles of all developer components is between about 0.5 and about 2.

15. In a hair dyeing preparation comprising at least one coupler component and at least one developer component in a suitable cosmetic carrier, the improvement wherein (a) said at least one coupler component comprises a compound according to claim 2 in a quantity of 0.05 to 10 millimole per 100 g of the hair dyeing preparation, (b) said at least one developer component comprises a compound selected from the group consisting of 2,4,5,6-tetraaminopyrimidine and salts thereof, p-tolylenediamine and salts thereof, p-phenylenediamine and salts thereof, N,N-dimethyl-p-phenylenediamine and salts thereof, $N^1$-(2-methanesulfonamido)-ethyl-3-methyl-p-phenylenediamine and salts thereof, $N^1$-ethyl-$N^1$-(2-hydroxyethyl)-p-phenylenediamine and salts thereof, 2-chloro-p-phenylenediamine and salts thereof, and 2,5-diaminoanisole and salts thereof, and (c) the ratio between the number of moles of all coupler components and the number of moles of all developer components is between about 0.5 and about 2.

16. In a hair dyeing preparation comprising at least one coupler component and at least one developer component in a suitable cosmetic carrier, the improvement wherein (a) said at least one coupler component comprises a compound according to claim 1 in a quantity of 0.05 to 10 millimole per 100 g of the hair dyeing preparation, (b) said at least one developer component comprises a compound selected from the group consisting of 2,4,5,6-tetraaminopyrimidine and salts thereof, p-tolylenediamine and salts thereof, p-phenylenediamine and salts thereof, N,N-dimethyl-p-phenylenediamine and salts thereof, $N^1$-(2-methanesulfonamido)-ethyl-3-methyl-p-phenylenediamine and salts thereof, $N^1$-ethyl-$N^1$-(2-hydroxyethyl)-p-phenylenediamine and salts thereof, 2-chloro-p-phenylenediamine and salts thereof, and 2,5-diaminoanisole and salts thereof, and (c) the ratio between the number of moles of all coupler components and the number of moles of all developer components is between about 0.5 and about 2.

17. A hair dyeing preparation according to claim 16, wherein said suitable cosmetic carrier comprises an oil-in-water emulsion containing (a) from about 0.1 to about 25% by weight of a component selected from the group consisting of alcohols, hydrocarbons, and esters, all containing a straight chain $C_{12}$–$C_{18}$ alkyl group, and (b) from about 0.5 to about 30% by weight of an emulsifier selected from the group consisting of anionic, nonionic or ampholytic surfactants.

18. A hair dyeing preparation according to claim 15, wherein said suitable cosmetic carrier comprises an oil-in-water emulsion containing (a) from about 0.1 to about 25% by weight of a component selected from the group consisting of alcohols, hydrocarbons, and esters, all containing a straight chain $C_{12}$–$C_{18}$ alkyl group, and (b) from about 0.5 to about 30% by weight of an emulsifier selected from the group consisting of anionic, nonionic or ampholytic surfactants.

19. A hair dyeing preparation according to claim 14, wherein said suitable cosmetic carrier comprises an oil-in-water emulsion containing (a) from about 0.1 to about 25% by weight of a component selected from the group consisting of alcohols, hydrocarbons, and esters, all containing a straight chain about $C_{12}$–$C_{18}$ alkyl group, and (b) from about 0.5 to about 30% by weight of an emulsifier selected from the group consisting of anionic, nonionic or ampholytic surfactants.

20. A hair dyeing preparation according to claim 13, wherein said suitable cosmetic carrier comprises an oil-in-water emulsion containing (a) from about 0.1 to about 25% by weight of a component selected from the group consisting of alcohols, hydrocarbons, and esters, all containing a straight chain about $C_{12}$–$C_{18}$ alkyl group, and (b) from about 0.5 to about 30% by weight of an emulsifier selected from the group consisting of anionic, nonionic or ampholytic surfactants.

* * * * *

UNITED STATES PATENT AND TRADEMARK OFFICE
CERTIFICATE OF CORRECTION

PATENT NO. : 4,994,087
DATED : 2-19-91
INVENTOR(S) : Konrad et al.

It is certified that error appears in the above-identified patent and that said Letters Patent is hereby corrected as shown below:

At Claim 9, Column 11, line 59, "NB," should read --N,--.

At Claim 14, Column 12, line 59, "pphenylenediamine" should read --p-phenylenediamine--.

At Claim 14, Columne 12, line 64, "pphenylenediamine" should read --p-phenylenediamine--.

Signed and Sealed this

Fourth Day of August, 1992

Attest:

DOUGLAS B. COMER

*Attesting Officer*     *Acting Commissioner of Patents and Trademarks*